US012734122B2

(12) United States Patent
Raths et al.

(10) Patent No.: US 12,734,122 B2
(45) Date of Patent: Sep. 15, 2026

(54) PROCESS FOR PREPARING SURFACTANT SOLUTIONS WITH N-ACYL AMINO ACID SALTS

(71) Applicant: BASF SE, Ludwigshafen (DE)

(72) Inventors: Hans-Christian Raths, Düsseldorf (DE); Frank Clasen, Düsseldorf (DE); Ansgar Behler, Bottrop (DE)

(73) Assignee: BASF SE, Ludwigshafen am Rhein (DE)

(*) Notice: Subject to any disclaimer, the term of this patent is extended or adjusted under 35 U.S.C. 154(b) by 323 days.

(21) Appl. No.: 18/039,312

(22) PCT Filed: Nov. 24, 2021

(86) PCT No.: PCT/EP2021/082849
§ 371 (c)(1),
(2) Date: May 30, 2023

(87) PCT Pub. No.: WO2022/117415
PCT Pub. Date: Jun. 9, 2022

(65) Prior Publication Data

US 2024/0000686 A1 Jan. 4, 2024

(30) Foreign Application Priority Data

Dec. 1, 2020 (EP) .................................... 20210866

(51) Int. Cl.
*A61K 8/44* (2006.01)
*A61Q 19/10* (2006.01)

(52) U.S. Cl.
CPC ................ *A61K 8/44* (2013.01); *A61Q 19/10* (2013.01); *A61K 2800/5426* (2013.01); *A61K 2800/596* (2013.01); *A61K 2800/80* (2013.01)

(58) Field of Classification Search
CPC .............. A61K 8/44; A61K 2800/5426; A61K 2800/596; A61K 2800/80; A61Q 19/10; C07C 231/02; C11D 3/2065; C11D 3/2079; C11D 3/33; C11D 11/0094; C11D 11/04; C11D 1/10
See application file for complete search history.

(56) References Cited

U.S. PATENT DOCUMENTS 3,836,551 A 9/1974 Schroeder et al.
4,380,646 A 4/1983 Franzmann
5,898,084 A * 4/1999 Oftring ................ C07C 231/02 562/524
2006/0116305 A1 6/2006 Yamato et al.
2008/0008672 A1 1/2008 Tobita
2015/0126776 A1* 5/2015 Wang .................... C07C 231/10 562/553
2016/0152555 A1* 6/2016 Wang .................... C07C 233/47 554/63
2019/0091124 A1* 3/2019 Nahrwold ............ C07C 231/02

FOREIGN PATENT DOCUMENTS

| | | | | |
|---|---|---|---|---|
| EP | 2736878 B1 | 6/2016 | | |
| EP | 2870136 B1 | 10/2018 | | |
| JP | 11-508598 A | 7/1999 | | |
| JP | 2008-013513 A | 1/2008 | | |
| JP | 2011-001374 A | 1/2011 | | |
| JP | 2014-527519 A | 10/2014 | | |
| JP | 2016-528284 A | 9/2016 | | |
| KR | 10-2017-0042140 A | 4/2017 | | |
| KR | 2019-0024334 A | 3/2019 | | |
| WO | 95/07882 A1 | 3/1995 | | |
| WO | WO-9507881 A1 * | 3/1995 | ........... | C07C 231/02 |
| WO | WO-96/09278 A1 | 3/1996 | | |
| WO | WO-9703043 A1 * | 1/1997 | ............. | C09K 23/00 |
| WO | WO-2015/026538 A1 | 2/2015 | | |
| WO | 2017/061759 A1 | 4/2017 | | |

OTHER PUBLICATIONS

Lanigan et. al. “Final report on the safety assessment of Methyl Alcohol” Int J Toxicol 2001:20 Suppl 1:57-85. (Year: 2001).*
TCI. “Condensing Agents” 2018. (Year: 2018).*
Korting “Liquid Jet Vacuum Ejectors”, 2010. (Year: 2010).*
Griffin. Advanced Dryness Detection for Improved Throughput and Yield during Evaporation. American Laboratory, 2006. (Year: 2006).*
WO9703043A1—machine translation provided. Oftring. “Process for Preparing N-Acylaminocarboxylic Acids and N-Acylaminosulphonic Acids and the Alkali Metal Salts Thereof.” (Year: 1997).*
Lanigan “Final report on the safety assessment of Methyl Alcohol” Int J Toxicol 2001. (Year: 2001).*
WO9703043A1—machine translation. “Process for Preparing N-Acylaminocarboxylic Acids and N-Acylaminosulphonic Acids and the Alkali Metal Salts Thereof” 1997 (Year: 1997).*

(Continued)

*Primary Examiner* — Ali Soroush
*Assistant Examiner* — Rajan Pragani
(74) *Attorney, Agent, or Firm* — Faegre Drinker Biddle & Reath LLP

(57) ABSTRACT

The invention relates to a process for preparing surfactant solutions with N-acyl amino acids or their salts and to surfactant solutions with N-acyl amino acids or their salts obtained by the inventive process. The invention relates further to cosmetic or detergent cleaning compositions comprising solutions with N-acyl amino acids or their salts obtained by the process.

18 Claims, No Drawings

(56) References Cited

OTHER PUBLICATIONS

WO9703043A1—machine translation. Oftring "Process for Preparing N-Acylaminocarboxylic Acids and N-Acylaminosulphonic Acids and the Alkali Metal Salts Thereof" 1997 (Year: 1997).*
International Preliminary Report on Patentability received for PCT Patent Application No. PCT/EP2021/082849, mailed on Jun. 15, 2023, 10 pages.
European Search Report for EP Patent Application No. 20210866.8, Issued on Jun. 4, 2021, 3 pages.
International Application No. PCT/EP2021/082849, International Search Report and Written Opinion, mailed Mar. 7, 2022.
He, et al., Chapter 2: Basic Operations of Organic Chemistry Experiments, Organic Chemistry Experiments, Huazhong University of Science and Technology Press, Aug. 2012, p. 65.

* cited by examiner

PROCESS FOR PREPARING SURFACTANT SOLUTIONS WITH N-ACYL AMINO ACID SALTS

CROSS-REFERENCE TO RELATED APPLICATIONS

This is the U.S. national phase of International Application No. PCT/EP2021/082849, filed Nov. 24, 2021, which claims the benefit of European Patent Application No. 20210866.8, filed Dec. 1, 2020.

FIELD OF THE INVENTION

The invention relates to a process for preparing surfactant solutions with N-acyl amino acids or their salts and to surfactant solutions with N-acyl amino acids or their salts obtained by the inventive process. The invention relates further to cosmetic or detergent cleaning compositions comprising solutions with N-acyl amino acids or their salts obtained by the process.

PRIOR ART

N-Acyl amino acid salts are anionic surfactants useful in laundry detergents, household or industrial cleaners, foamers, emulsifiers, personal cleansers, and other applications. Because they are often exceptionally mild, the salts are particularly valuable for personal care formulations.

In general, N-acyl amino acid salts have been underutilized, due at least in part to challenges in manufacturing them. N-Acyl amino acid salts can be made from the corresponding fatty acyl chlorides and amino acid salts using Schotten-Baumann chemistry, but this process is expensive and generates an equimolar amount of undesirable salt by-product. In an alternative synthetic method, a fatty acid is reacted with an amino alcohol to give a fatty amide, which is then oxidized to give the N-acyl amino acid. This process is hampered by relatively low yields, low selectivity in the oxidation step, the use of precious metal catalysts, and the need for a conventional organic workup. In other known processes, the N-acyl amino acid salt is made from a fatty acid. For example, U.S. Pat. No. 3,836,551 teaches to react fatty acids with amino acid salts either in the molten fluid phase (i.e., without a solvent), in solution using a polar aprotic solvent (such as dimethyl sulfoxide or N,N-dimethylformamide), or in suspension with a nonpolar organic solvent (e.g., xylene). Typical reaction times are about 9 hours, and by-products are not discussed. Generally, the fatty acid route is also less preferred because it requires a high reaction temperature, which leads to undesirable color development in the N-acyl amino acid salt. Fatty esters have also been used as starting materials. WO96/09278 teaches to react a fatty alkyl ester (e.g., methyl oleate) with an amino acid salt and a 30-150% molar excess of a strong base (e.g., sodium methoxide/methanol solution). Sodium sarcosinate is used in the examples, although other amino acid salts are taught as suitable, and no vacuum is used. U.S. Pat. No. 4,380,646 discloses the preparation of an acylated amino carboxylic acid comprising contacting an amino carboxylic acid, its alkali metal or alkaline earth metal salt with a low alkyl carboxylic acid ester in the presence of an alkali metal or alkaline earth metal alcoholate.

WO97/03043 describes the preparation of N-acyl amino acid salts by reacting a mono-, di-, or triglyceride with an amino acid salt in the presence of a strong base. In the examples, colza oil (a triglyceride) is reacted with sodium sarcosinate in the presence of sodium methoxide/methanol, and the reaction continues under water jet vacuum until glycerides are no longer detected. A typical organic workup follows. The reference indicates that the glycerin produced in the course of the reaction either remains in the reaction mixture or is partly or wholly removed in the conventional workup. At the conclusion of the reaction, the mixture is typically a viscous paste.

The preparation of N-acyl amino acid salts is particularly challenging when the reactants are fatty alkyl esters and alkali metal glycinates, as in the preparation of sodium cocoyl glycinate, sodium myristyl glycinate, or sodium lauryl glycinate. This reaction is troublesome due to a lack of reagent compatibility, solidification of the reaction mixture at elevated process temperatures, color development, severe foaming during methanol removal, and significant by-product generation. Solvents have been used to mitigate some of these concerns but typically in the context of sarcosinates or other amino acid salts that are more easily converted to N-acyl amino acid salts. Moreover, the need to remove a solvent introduces additional challenges. EP2870136B1 describes two different processes for preparing N-acyl amino acid salts. According to one process a fatty alkyl mono ester is reacting with an amino acid salt in the presence of a polyol selected from the group of glycerin and propylene glycol and a C1-C4 alkanol, wherein the alkanol is removed from the reaction mixture as it forms, wherein the polyol is used in an amount effective to keep the reaction mixture fluid until conversion reaches a level of completion in the range of 50-90 mole %. According to a second process a polyol ester selected from mono-, di- or triglycerides is reacting with an amino acid salt in the presence of an added polyol selected from the group of glycerin and propylene glycol and when the conversion is in the range of 50 to 90 mol %, water is added. Both processes describe the need of adding a polyol, which remains in the surfactant mixture, which is not desired for all applications. EP2736878B1 discloses a similar process, wherein glycine or a salt thereof is reacting with a fatty acid ester in a medium selected from the group consisting of glycerol, propylene glycol and combinations thereof, and wherein the mixture has a pKa ranging from 9.5 to 13. Even after this process the glycerol remains in the reaction mixture.

KR 20190024334 describes an environmentally friendly process for preparing acyl glycinates and cleaning compositions comprising them. In a first step an alkali metal alkoxide was prepared by reacting a metal hydroxide with alcohol like methanol under removing of water e.g. by vacuum. In a second reaction step the alkali metal alkoxide, a solvent and a mixture of glycine and fatty acid ester were heated to about 135° C. After the reaction was terminated the removed water from step 1 was added. The result is a clear yellow liquid phase. According to the application the reactivity of the reaction in step 2 is increased by using one or more polyhydric solvents such as glycerin or glycols which does not volatilize during the reaction. The polyols remain in the surfactant mixture and are difficult to remove without altering the surfactant mixture.

WO2015/026538 claims a process for preparing N-acyl amino acid salts by reacting a fatty alkyl ester with an amino acid salt in the presence of an alkoxide catalyst at a pressure of at least 5 psig. According to one example methyl laurate was mixed with an amino acid salt and a solution of alkali alkoxides in methanol and sealed and heated to 130° C. at 7 to 50 psig in a reactor.

US200080008672 claims a creamy wash composition comprising A) a N-long chain acyl acidic amino acid, B) one polyhydric alcohol, C) a nonionic-surfactant, D) a salt of a divalent or higher cation and E) water. According to example 2 the wash composition comprising 30 wt % glycerol, about 18.20 wt % N-acyl glutamate and/or alaninate.

In sum, an improved process for making aqueous solutions of N-acyl amino acid salts is needed. In particular, the industry needs a more sustainable process without using acid chlorides for converting the amino acid. The improved process should show at the same time high yields and resource-saving properties like avoiding salt generation, high temperatures, long reaction times, high amounts of solvents like organic solvents or glycerin or propylene glycol. Moreover, it is preferred to have a simple one pot process starting from a low processed renewable raw material like a natural triglyceride. In addition, the improved process should lead to products that can be highly concentrated and are easy to formulate as a highly concentrated solution.

DESCRIPTION OF THE INVENTION

In a first aspect, the invention provides a process for preparing surfactant solutions with N-acyl amino acids or their salts comprising the steps a) preparing an alkali metal salt of an amino carboxylic acid in-situ by reacting amino carboxylic acid and an alkali metal methoxide by a1) reacting an amino carboxylic acid with a solution consisting of alkali metal methoxide in methanol in presence of carboxyl glyceride ester or by a2) reacting an amino carboxylic acid with a solution consisting of alkali metal methoxide in methanol and afterwards adding carboxyl glyceride ester before
b) forming the N-acyl amino acid salts by reacting said alkali metal salt of amino carboxylic acid with carboxyl glyceride ester by heating and under removal of methanol until at least 60 wt % of the theoretical amount of methanol was removed and
c) afterwards applying vacuum and
d) after releasing vacuum adding water to form solutions with N-acyl amino acids salts
e) and optional adjusting pH-values.

The process of the present invention performs particularly well as the amino carboxylic acid salts are prepared in-situ. An in-situ preparation means, that the product is used for a following chemical reaction immediately after producing without separation, purification or other recovery processes for the product. According to the invention it is beneficial that the amino carboxylic acid salts are produced and used for a following chemical reaction immediately after it is preparing, preferred without reprocessing, purification or other recovery processes, in particular for a following chemical reaction with carboxyl glyceride esters in the same reaction vessel. In comparison examples it has been shown that the process with the in-situ preparation of alkali metal salt of an amino carboxylic acid is extremely advantageous and much better for the yields than the use of the alkali metal salt of an amino carboxylic acid that can be purchased on the market, in view of better yields.

Additionally, the present invention performs particularly well, when after initial removal of methanol in step b) vacuum is applied.

Amino Carboxylic Acids

According to the invention aliphatic amino carboxylic acids having from 2 to 10 carbon atoms are suitable, preferably from 3 to 6 carbon atoms, more preferable aliphatic amino carboxylic acids selected from the group consisting of valine, leucine, Isoleucine, glycine, methionine, alanine, 3-alanine, sarcosine (N-methylglycine), aspartic acid (asparagine), threonine or glutamic acid, especially preferred from the group consisting of alanine, glycine, threonine and asparagine. In particular, glycine is the preferred aliphatic amino carboxylic acid according to the invention.

Carboxylic Glyceride Ester

According to the invention the wording "carboxylic glyceride" or "carboxylic glyceride ester" means ester of glycerol and carbon acids (so-called carboxylic acid). The glycerol is esterified with, respectively, one, two and/or three carboxylic acids (mono-, di or triglyceride ester of carboxylic acids). Di- or triglycerides may be ester of glycerol esterfied with two or three identical or different carboxylic acids. Suitable carboxylic glycerides include in particular naturally occurring fatty acid glycerides. These are usually mono-, di- or in particular triglycerides of saturated or unsaturated monocarboxylic acids having from 6 to 30, in particular from 6 to 22, carbon atoms, or mixtures thereof. Preferred according to the invention carboxyl glyceride ester are selected from fatty acid glyceride ester, preferably from glyceride ester of fatty acids with 6 to 22 carbon atoms. Examples of the underlying monocarboxylic (fatty) acids are lauric acid, myristic acid, palmitic acid, stearic acid, oleic acid, linoleic acid and linolenic acid. Preferred are naturally fatty acid glyceride ester and in particular triglycerides, especially preferred are vegetable or animal fats or oils. Examples of such suitable triglycerides are groundnut oil, linseed oil, rapeseed oil, copra oil, palm fruit oil, coconut oil or palm kernel oil, castor oil, bovine tallow soybean oil, colza oil, olive oil, sunflower oil, cottonseed oil and fish oil. Most preferred according to the invention are carboxyl glyceride ester selected from the group consisting of coconut oil, in particular unhardened, refined coconut oil.

Details of the Process

We surprisingly found that N-acyl amino acids or their salts are prepared in higher yields, if carboxylic glycerides react with salts of amino carboxylic acids, which have been prepared in situ. The yield of obtained N-acyl amino acids or their salts are significant higher compared to a reaction of carboxylic glycerides with a common available salt of amino carboxylic acid.

Salts of amino carboxylic acids can be prepared by reacting amino carboxylic acids and alkali metal alkoxides, wherein the alkali metal alkoxides are preferable used as a solution in the corresponding alcohol.

According to one embodiment of the invention in step a) an alkali metal salt of an amino carboxylic acid is prepared in-situ by a1) reacting an amino carboxylic acid with a solution of alkali methoxide in methanol in presence of carboxyl glyceride ester. According to this embodiment a1) it is possible to add the amino carboxylic acid to a mixture consisting of alkali metal alkoxide in methanol and carboxylic glyceride or to add the solution of alkali metal alkoxide in methanol to a mixture of amino carboxylic acid and carboxylic glycerides.

According to another embodiment of the invention in step a) an alkali metal salt of an amino carboxylic acid is prepared in-situ by a2) reacting an amino carboxylic acid with a solution consisting of alkali metal methoxide in methanol, wherein according to a2) afterwards a carboxyl glyceride ester was added before step b). According to this embodiment a2) it is possible to add the amino carboxylic acid to the solution of alkali metal alkoxide in methanol for reacting or to add the solution of alkali metal alkoxide to the amino carboxylic acid for reacting and in both options afterwards adding the carboxylic glyceride before step b)

According to the invention a process is preferred wherein the alkali metal salt of an amino carboxylic acid is prepared in-situ by a1) reacting an amino carboxylic acid with a solution consisting of alkali metal methoxide in methanol in presence of carboxyl glyceride ester. According to this embodiment a1) it is preferred to add the solution of alkali metal alkoxide in methanol to a mixture of amino carboxylic acid and carboxylic glyceride ester.

However, according to both embodiments the process of the present invention performs likewise particularly well when the alkali metal salt is prepared in-situ by a1) or a2) using a solution of about 20 to 35 wt % alkali metal methoxide in methanol, especially of about 25 wt % sodium methoxide in methanol.

It is preferred to use in a1) or a2) alkali methoxide in methanol, wherein the alkali is selected from the group consisting of sodium and kalium, more preferably from the group consisting of sodium.

The process according to the present invention performs well when the alkali metal salt of amino carboxylic acid is prepared by a1) or a2) reacting amino carboxylic acid in a relative mole ratio of amino carboxylic acids to alkali metal methoxide in the range from about 3:1 to 1:3, preferably in the range from 1:1.3 to 1:1 and more preferably in the range of about 1:1.

According to both embodiments a1) or a2) the salts of amino carboxylic acids are preferred prepared by reacting an amino carboxylic acid with an alkali metal methoxide under stirring until homogenization, preferably under stirring at temperatures in the range of 30-60° C., in particular in the range of 35 to 45° C. According to both preferred embodiments the resulted salts of amino carboxylic acids are formed as an insoluble precipitate, which is very finely distributed.

According to the invention the salts of amino carboxylic acids are prepared in-situ and used for a following chemical reaction with the carboxylic glycerides immediately without separation, purification or other recovery processes after step a) and before step b).

In step b) N-acyl amino acid salts are formed by reacting carboxylic glyceride ester and the salts of amino carboxylic acids. Reaction step b) is carried out by heating and under removal of methanol until at least 60% by weight ("60 wt %") of the theoretical amount of methanol. For the reaction step b) it is preferred that the reaction takes place by heating at a temperature above 100° C., preferably in the range of 120 to 170° C. and preferred 130 to 160° C.

The carboxylic glyceride ester and the salts of amino carboxylic acids are preferred present in a relative mole ratio of fatty acid:amino carboxylic acid in the range from 1:2 to 2:1, more preferred from 0.9:1 to 1.1:1 and in particular in a relative mole ratio of about 1:1—based on fatty acid of carboxyl glyceride ester.

The removal of methanol in step b) is done preferred under atmospheric air pressure, i.e. not with artificially increased or reduced air pressure, and especially by continuous distillation for example via distillation bridge and condensing with a water-cooled condenser. It is preferred to remove methanol in a distillation bridge at a head temperature of about 65° C., i.e. its boiling point. The reaction is preferably carried out until the head temperature in the distillation bridge clearly falls below the boiling point of methanol. This can take about 1 to 16 hours, preferable 1 to 8 hours, at normal pressure.

It is preferred that the reaction step b) is carried out until at least 60% by weight ("60 wt %") of the theoretical amount of methanol is distilled off. Preferably the reaction step b) is carried out until 65 to 90 wt %, of the theoretical amount is distilled off. The theoretical amount includes both the quantity of methanol used as solvent in the solution and the quantity of methanol formed from the alkali metal methoxide.

According to the invention the process comprises an additional step c) afterwards a) and b), i.e. after at least 60 wt % of the theoretical amount of methanol was removed vacuum was applied.

It is beneficial to have a vacuum in the range of about 100 to 400 mbar, preferably 250-350 mbar, and especially about 300 mbar. The additional step c) is preferably carried out preferred at temperatures in the range of 120 to 170° C., more preferred of 130 to 160° C. and especially preferred for about 0.5 to 8 hours, especially until the head temperature of the distillation bridge drops to a temperature in the range of 20-40° C.

The reaction step c) is preferably carried out until at least 95 wt %, more preferably about 100 wt % of the theoretical amount of methanol has been removed.

The reaction time depends on size, geometry and heating system and might differ from this example. In a preferred embodiment the reaction including steps a), b) and c) needs about 1.5 to 24 hours, preferred 1.5 to 16 hours and more preferred 2 to about 4 hours.

According to the process in step d) water is added to convert the reaction product into an aqueous solution after releasing the vacuum, especially by inserting nitrogen. According to the invention it is preferred to add water at temperatures in the range of 90 to 130° C., while the mixture still remains stirrable. At lower temperature it takes a longer time to dissolve the material. Preferably water is added very slowly to the reaction mixture at temperatures in the range of 90 to 130° C. It is preferred that in d) the water is added in such an amount that solutions of about 20 to 70 wt %, especially 25 to 55 wt % and more preferred 25 to 40 wt % comprising N-acyl amino acids or their salts are obtained.

The pH of the solution typically ends up in the range of 8-12, preferably 9-11 and can be additionally adjusted, if desired, by adding caustic soda or by adding an acid, preferably by adding citric acid, after step d). Preferably in step the pH value is adjusted after cooling and especially step e) is omitted.

The yields of N-acyl amino acids or their salts are very high, in general greater than 70 mol %, preferable greater than 80 mol %, most preferable in the range of 80-90 mol %—based on amino acids.

According to the process of the invention no additional solvents or liquids like polyvalent alcohols as glycerol or propylene glycol or other solvents or liquids like known state of the art are used. This is a great advantage for use in cosmetic applications where glycerol or propylene glycol are not desired.

Additionally, according to the invention no additional catalysts like the known state of the art is needed or used in the process.

It is an advantageous according to the invention that no work-up workflows are needed and/or used, e.g. for improving the yields or for reducing undesirable by-products, follows step e) to obtain N-acyl amino acids or their salts One special and preferred embodiment of the invention is relating to a process for preparing a surfactant solution with N-cocoyl glycinate or its salts. According to this special embodiment in step a) a sodium salt of glycine is prepared by a1) reacting glycine with a solution consisting of sodium methoxide in methanol in presence of coconut oil, wherein the solution of sodium methoxide in methanol was added to glycine and coconut oil. In step b) this reaction mixture comprising the in-situ prepared salts of amino carboxylic acids and carboxylic glyceride ester is heated to temperatures in the range of 120 to 170° C., preferred 130 to 160° C. to form the N-cocoyl glycinate. After about 60 to 80% by weight of the theoretical amount methanol is distilled off at atmospheric pressure. Afterwards in step c) vacuum is applied in the range of 100 to 400 mbar until no methanol is removed anymore. All in all, the reaction needs about 2 to 4, preferred about 3 hours. Afterwards the vacuum is released/lifted and the temperature is cooled down preferably to about 110° C. water is added in step d), preferable in such an amount that a solution with about 30 wt % is obtained. The yields of sodium salt of N—C8-C18 cocoyl glycinate is in the range of 80-90 mol %—based on glycine.

In a second aspect, the invention provides surfactant solutions with N-acyl amino acids or their salts prepared according claim 1 consisting of 0.1 to 4 wt % amino acids
0.1 to 7.5 wt % fatty acids
0.1 to 7 wt % glycerol
20.0 to 70.0 wt % N-acyl amino acids or their salts
0 to 15 wt % by-products selected from the group consisting of glycerol mono fatty acid ester, glycerol di fatty acid ester and/or methyl esters of fatty acids and water in such an amount that the sum of the components is 100 wt %.

According to the invention "wt %" means "% of weight".

Preferred are surfactant solutions with N-acyl amino acids or their salts prepared according claim 1 consisting of 0.5 to 4 wt % amino acids
3.0 to 7.5 wt % fatty acids
2.0 to 7.0 wt % glycerol
25.0 to 55.0 wt % N-acyl amino acids or their salts
0 to 15 wt % by-products selected from the group consisting of glycerol mono fatty acid ester, glycerol di fatty acid ester and/or methyl esters of fatty acids and water in such an amount that the sum of the components is 100 wt %.

It may be possible that the solutions are comprising further by-products like glycerol mono fatty acid ester and/or glycerol di fatty acid esters (so-called partial glycerides), but preferable in amounts less than 10 wt %, most preferable between 0.1 and 10 wt %.

Further aspects of the invention are relating to cleaning compositions for detergents and/or personal cosmetics comprising surfactant solutions with N-acyl amino acids or their salts prepared according claim 1 and to cleaning compositions for detergents and/or personal cosmetics comprising surfactant solutions, especially according to the preferred surfactant solutions defined above.

Cleaning Compositions

Cleaning compositions for detergents and/or personal cosmetics are to be understood here as all compositions known to a person skilled in the art which are exclusively or primarily intended to be applied externally to the human body or hair for the cleaning, caring, protection, and maintaining of a good condition, perfuming, changing the appearance or for influencing. Preferably the surfactant solutions are used for personal care compositions, in particular surface-active personal care compositions, such as cleaning compositions for personal care cosmetics, for example, foam baths, shower gels, shower baths, shower milks, shower creams, shampoos, hair masks, hair milks and hair conditioners.

Preferably the cleaning compositions for personal care compositions comprising—based on weight (wt) % in personal care composition comprising A) 1.0 to 30 wt %, especially 1.0 to 25 wt %, N-Acyl amino acids or their salts obtained according to claim 19
B) 1.0 to 30 wt %, especially 5.0 to 25.0 wt % one or more detersive surfactants selected from the groups selected anionic surfactants, nonionic surfactants, amphoteric and/or zwitterionic surfactants, wherein the anionic surfactants are different from the surfactant solutions as obtained according claim 1
C) 0 to 5 wt %, especially 0.01 to 1 wt % cationic polymers,
D) up to 100 wt % other components, different from A), B) and/or C).

Preferred are personal care compositions—based on weight (wt) % in personal care composition comprising A) 1.0 to 30 wt %, especially 1.0 to 25 wt % N-Acyl amino acids or their salts obtained according to claim 1
B) 1.0 to 30 wt %, especially 5.0 to 25.0 wt % one or more detersive surfactants selected from the groups selected anionic surfactants, nonionic surfactants, amphoteric and/or zwitterionic surfactants, wherein the anionic surfactants are different from the surfactant solutions as obtained according claim 1
C) 0 to 5 wt %, especially 0.01 to 1 wt % cationic polymers,
D) up to 100 wt % other components, different from A), B) and/or C).

A) Anionic Surfactants, Nonionic Surfactants, Amphoteric and/or Zwitterionic Surfactants Examples of anionic surfactants are soaps, alkyl benzenesulfonates, alkane sulfonates, olefin sulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and di alkyl sulfosuccinates, mono- and di alkyl sulfosuccinamates, sulfotriglycerides, amide soaps, ether carboxylic acids and salts thereof, fatty acid isethionates, fatty acid taurides, alkyl oligo glucoside sulfates, protein fatty acid condensates (particularly wheat-based vegetable products) and alkyl (ether) phosphates. If the anionic surfactants contain polyglycol ether chains, the polyglycol ether chains may have a conventional homolog distribution, although they preferably have a narrow homolog distribution. Particularly suitable anionic surfactants in the preparations according to the invention are alkyl ether sulfates.

Alkyl ether sulfates ("ether sulfates") are known anionic surfactants which, on an industrial scale, are produced by $SO_3$ or chlorosulfonic acid (CSA) sulfation of fatty alcohol or oxoalcohol polyglycol ethers and subsequent neutralization. The ether sulfates may have both a conventional homolog distribution and a narrow homolog distribution. It is particularly preferred to use ether sulfates based on adducts of, on average, 1 to 6 mol and preferably 1 to 3 mol ethylene oxide with technical $C_{12/14}$ or $C_{12/18}$ coconut fatty alcohol fractions in the form of their sodium and/or magnesium salts.

Further anionic surfactants useful within the context of the present invention are alpha-sulfo fatty acid di salts according to the formula (I) specified above

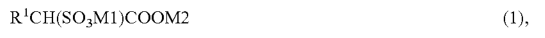

$$R^1CH(SO_3M1)COOM2 \quad (1),$$

in which the radical $R^1$ is a linear or branched alkyl or alkenyl radical having 6 to 18 carbon atoms and the radicals M1 and M2—independently of one another—are selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine.

In a preferred embodiment, the radical $R^1$ in the formula (I) is a saturated, linear alkyl radical having 10 to 16 carbon atoms. The radicals M1 and M2 in formula (I) are preferably selected from the group comprising H (hydrogen) and Na (sodium).

The compounds can be prepared by all methods known appropriately to those skilled in the art. A particularly preferred method of preparation here is the sulfation of the corresponding carboxylic acids. Here, the corresponding carboxylic acid and in particular the corresponding fatty acids are reacted with gaseous sulfur trioxide, the sulfur trioxide being used preferably in an amount such that the molar ratio of $SO_3$ to fatty acid is in the range from 1.0:1 to 1.1:1. The crude products obtained in this way, which are acidic sulfation products, are then partially or completely neutralized, preference being given to complete neutralization with aqueous NaOH. If desired, it is also possible to undertake purification steps and/or a bleaching (for adjusting the desired pale color of the products).

Preferred alpha-sulfo fatty acid di salts are technical-grade mixtures of the alpha-sulfo fatty acid desalts, which is commercially available as Texapon® SFA from BASF Personal Care Nutrition GmbH.

In addition, amphoteric and/or zwitterionic surfactants may be used in addition with or instead of the anionic surfactants. Suitable amphoteric and/or zwitterionic surfactants are betaine surfactants according to formula (II) and/or (Ill) are useful and in particular the condensation product of $C_{8/18}$ cocofatty acid-N,N-dimethyl aminopropyl amide with sodium chloroacetate known under the CTFA name of Cocamidopropyl Betaine is preferred.

Betaines are known surfactants which are mainly produced by carboxyalkylation, preferably carboxymethylation, of aminic compounds. The starting materials are preferably condensed with halocarboxylic acids or salts thereof, more particularly with sodium chloroacetate. Examples of suitable betaines are the carboxyalkylation products of secondary and, in particular, tertiary amines corresponding to formula (II):

(II)

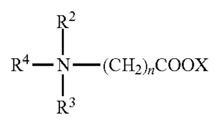

in which $R^4$ stands for alkyl and/or alkenyl groups containing 6 to 22 carbon atoms, $R^2$ stands for hydrogen or alkyl groups containing 1 to 4 carbon atoms, $R^3$ stands for alkyl groups containing 1 to 4 carbon atoms, n is a number of 1 to 6 and X is an alkali metal and/or alkaline earth metal or ammonium. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, $C_{12/14}$ cocoalkyl dimethyl amine, myristyl dimethyl amine, cetyl dimethyl amine, stearyl dimethyl amine, stearyl ethyl methyl amine, oleyl dimethyl amine, $C_{16/18}$ tallow alkyl dimethyl amine and technical mixtures thereof.

Other suitable betaines are carboxylation products of amidoamines corresponding to formula (III):

(III)

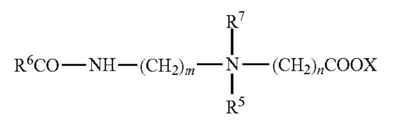

in which $R^6CO$ is an aliphatic acyl group containing 6 to 22 carbon atoms and 0 or 1 to 3 double bonds, m is a number of 1 to 3, $R^7$ represents hydrogen or $C_{1-4}$ alkyl groups, $R^5$ represents $C_{1-4}$ alkyl groups, n is a number of 1 to 6 and X is an alkali metal and/or alkaline earth metal or ammonium. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethyl aminoethyl amine, N,N-dimethyl aminopropyl amine, N,N-diethyl aminoethyl amine and N,N-diethyl aminopropyl amine which are condensed with sodium chloroacetate. It is preferred to use a condensation product of $C_{8/18}$ cocofatty acid-N,N-dimethyl aminopropyl amide with sodium chloroacetate known under the CTFA name of Cocamidopropyl Betaine. Betaines distinguished by high purity are particularly preferred; in other words, low-salt betaines with a maximum salt content of 13% by weight, preferably 11% by weight and more particularly 7% by weight—based on active substance—are used. The corresponding salt is dependent on the production of the amphoteric surfactant; in the most common case, it is sodium chloride. In a particularly preferred embodiment, these betaines also have a low content of free fatty acids of at most 4% by weight and preferably at most 3% by weight, based on active substance.

Furthermore, imidazolinium betaines are also included. These substances are also known substances which can be obtained for example by cyclizing condensation of 1 or 2 mol of fatty acid with polyfunctional amines such as, for example, aminoethylethanolamine (AEEA) or diethylenetriamine. The corresponding carboxyalkylation products are mixtures of different open-chain betaines. Typical examples are condensation products of the abovementioned fatty acids with AEEA, preferably imidazolines based on lauric acid or again $C_{12/14}$-coconut fatty acid which are subsequently betainized with sodium chloroacetate.

Suitable Cocoamidopropyl Betaine are commercially available like Dehyton® PK 45 (supplied by BASF Personal Care and Nutrition GmbH).

In addition, nonionic surfactants may be used in addition with or instead of the anionic surfactants, amphoteric or zwitterionic surfactants. Suitable nonionic surfactants are selected from the group consisting of fatty alcohol polyglycol ether, ethoxylated fatty acid glycerol ester; mixed ethers or mixed formals; polysorbates and sugar-based carbohydrates.

In particular, alk(en)ylpolyglucosides are preferred examples for sugar-based carbohydrates.

Alkyl polyglycosides are known nonionic surfactants which have in particular the formula (IV),

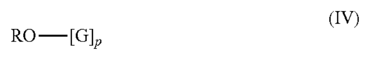

(IV)

in which

R is an alkyl radical having 6 to 22 carbon atoms,

G is a sugar radical having five or six carbon atoms and p is a number from 1 to 10.

They can be obtained by the relevant methods of preparative organic chemistry. The alkyl polyglycosides can be derived from aldoses or ketoses having 5 or 6 carbon atoms, preferably from glucose. The preferred alkyl polyglycosides are therefore alkyl polyglucosides. The index number p in the general formula (IV) specifies the degree of polymerization (DP), i.e. the distribution of mono- and polyglycosides, and is a number between 1 and 10. Whereas p in a given compound must always be an integer and can here in particular assume the values p=1 to 6, the value p for a particular alkyl polyglycoside is an analytically determined calculated parameter which in most cases is a fraction. Preferably, alkyl polyglycosides are used with an average degree of polymerization p of 1.1 to 3.0. Preference is given to those alkyl polyglycosides, from a technical applications point of view, for which the degree of polymerization is less than 1.7 and is particularly between 1.2 and 1.7.

The alkyl radical R can be derived from primary alcohols having 6 to 22, preferably 6 to 18 carbon atoms. Typical examples are caproic alcohol, caprylic alcohol, capric alcohol, decyl alcohol and undecyl alcohol, and also their technical grade mixtures, as obtained, for example, in the hydrogenation of technical grade fatty acid methyl esters or during the hydrogenation of aldehydes from Roelen's oxo synthesis. The alkyl radical R can also be derived from lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and also technical grade mixtures thereof.

In the context of the present invention, preference is given in particular to mixtures of different alkyl polyglycosides of the formula (IV), in which R is derived from primary alcohol mixtures. According to one preference R is derived from primary alcohol mixtures comprising 10 to 50% by weight 8 and 10 carbon atoms and 50 to 90% by weight 12 to 16 carbon atoms.

According to another preference R is derived from primary alcohol mixtures comprising 75 to 95% by weight primary higher alcohols with 10 to 22 carbon atoms, especially derivated from fatty acid mixture obtained from coco nut, preferably 12 to 16 carbon atoms.

Suitable products are Plantacare® 2000 and Plantacare® 818, both available by BASF.

It is preferred to use amounts from 1.0 to 30 wt %, especially 5.0 to 25.0 wt %, anionic surfactants, amphoteric and/or zwitterionic surfactants and/or nonionic surfactants—based calculated as active matter ad in respect to the personal care composition.

B) Cationic Polymers

Cationic polymers are known deposition agents, i.e. by using them in the personal care composition they deposit on skin and/or hair and give them a pleasant and a soft feeling. However, personal care compositions containing cationic polymers like cationic guar polymers have problems with their stability in case of presence of the wax dispersions as the wax(es) tend(s) to sediment more readily, probably a consequence of the deposition properties of the cationic polymers.

Preferred personal care composition also comprises a cationic polymer. These cationic deposition polymers can include at least one of a cationic guar polymer, a cationic non-guar galactomannan polymer, a cationic tapioca polymer, a cationic copolymer of acrylamide monomers and cationic monomers, and/or a synthetic, non-crosslinked, cationic polymer. Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, Amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol®A-15, Mirapol® AD-1, Mirapol® AZ1 of Miranol.

Especially, the personal care composition may comprise cationic polymer selected from the group consisting of cationically modified cellulose derivatives, PQ 10, PQ 67, cationically modified guar derivatives, such as, for example, Dehyquart® Guar N, guar hydroxypropyltrimonium chloride, cationic homo- or copolymers based on acrylamide, cationic homo- or copolymers based on vinyl pyrrolidone, cationic homo- or copolymers based on quaternized vinyl imidazole and cationic homo- or copolymers based on methacrylates.

In particular, cationically modified guar derivates, preferably Guar Hydroxypropyltrimonium Chloride, are present.

It is preferred to use amounts from 0 to 5 wt %, especially 0.01 to 1.0 wt % cationic polymers-based on the personal care composition.

C) Other Components

For an end-user application, the cosmetic formulations may comprise a series of further auxiliaries and additives, such as, for example, water, bodying agents, viscosity reducers, thickeners, salts, superfatting agents, stabilizers, polymers, fats, waxes, silicones, lecithins, protein hydrolyates, phospholipids, biogenic active ingredients, UV sunscreen factors, antioxidants, deodorants, antiperspirants, antidandruff agents, film formers, swelling agents, insect repellents, self-tanning agents, tyrosinase inhibitors (depigmenting agents), hydrotropes, solubilizers, preservatives, perfume oils, dyes, and the like, including water.

For reducing the viscosity, the personal care compositions may additionally contain polyols as an optional component.

Suitable polyols preferably contain 2 to 15 carbon atoms and at least two hydroxyl groups. The polyols may contain other functional groups, more especially amino groups, or may be modified with nitrogen. Typical examples are

- glycerol;
- alkylene glycols such as, for example, ethylene glycol, diethylene glycol, propylene glycol, butylene glycol, hexylene glycol and polyethylene glycols with an average molecular weight of 100 to 1.000 dalton;
- technical oligoglycerol mixtures with a degree of self-condensation of 1.5 to 10 such as, for example, technical diglycerol mixtures with a diglycerol content of 40 to 50% by weight;
- methylol compounds such as, in particular, trimethylol ethane, trimethylol propane, trimethylol butane, pentaerythritol and dipentaerythritol;
- lower alkyl glucosides, particularly those containing 1 to 8 carbon atoms in the alkyl group, for example methyl and butyl glucoside;
- sugar alcohols containing 5 to 12 carbon atoms, for example sorbitol or mannitol;
- sugars containing 5 to 12 carbon atoms, for example glucose or sucrose;
- amino sugars, for example glucamine;
- dialcoholamines, such as diethanolamine or 2-aminopropane-1,3-diol.

The polyols are used in quantities of typically 0.1 to 10% by weight, preferably 0.5 to 5% by weight and more particularly 0.7 to 3% by weight, based on the personal care composition. If larger quantities of polyol, preferably glycerol or ethylene glycol, are used, the solutions are stabilized against microbial infestation.

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons, for example squalane, squalene or dialkyl cyclohexanes.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Suitable thickeners are, for example, Aerosil types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. Typical examples of fats are glycerides while suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Salts like sodium chloride can be incorporated as a by-product.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Additionally, film formers may be present. Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof and similar compounds.

If desired, further protein hydrolyzates known from the prior art may be used, for example based on keratin such as the commercially available Nutrilan® Keratin W PP, or based on wheat, such as Gluadin® WLM Benz, Gluadin® WK or Gluadin® WP. It is also possible to add small amounts of free amino acids such as lysine or arginine.

Typical water-soluble additives are, for example, preservatives, water-soluble perfumes, pH regulators, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Suitable antidandruff agents are climbazol, octopirox and zinc pyrithione.

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

In addition, hydrotropes, for example ethanol, isopropyl alcohol or polyols, may be used to improve flow behavior.

Suitable preservatives are, for example, phenoxyethanol, formaldehyde solution, parabens, pentanediol or sorbic acid and the other classes of compounds known in the art. Suitable insect repellents are N,N-diethyl-m-toluamide, pentane-1,2-diol or Ethyl Butylacetylaminopropionate. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures:bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes which can be used are the substances approved and suitable for cosmetic purposes, as listed, for example, in the known publications. Examples are cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). As a luminescent dye, it is also possible for luminol to be present. These dyes are usually used in concentrations of from 0.001 to 0.1% by weight, based on the total mixture.

It is preferred to use these other components C) in amounts up to 100 wt %—based on the personal care composition.

EXAMPLES

Example 1a: Production of N-Acylated Amino Acids: Reaction of Glycine (=Amino Acid) with Coconut Oil (=Triglyceride) in the Presence of a Solution of Na-Methanolate in Methanol with Vacuum (Invention)

The reactor was charged with 22.5 g of glycine (0.3 mol) and 65.7 g of coconut oil (0.1 mol) and while stirring 64.8 g of a 25 wt % sodium methylate solution in methanol (0.3 mol sodium methylate) was added. While heating this heterogeneous mixture to 130-140° C., methanol was distilling off and was condensed with a water-cooled condenser. The temperature at the head of the distillation bridge rises to 65° C. As the methanol removal approached the end of the reaction 80 wt % methanol of the theoretical amount methanol, the temperature at the distillation bridge went down and the product mixture was well stirrable. In order to remove methanol completely from the reaction mixture additionally vacuum of 300 mbar was applied and further methanol was distilling of. The reaction mixture was getting very viscous during this stage. After total of 3 h the vacuum was then removed by inserting nitrogen and the mixture was diluted with water to give a roughly 30 wt % aqueous pale-yellow clear solution of sodium cocoyl glycinate. The temperature went down below 100° C. and the product was cooled down to ambient temperature staying a good stirrable clear solution. Analysis was done by liquid chromatography and gave 87.2 mol % yield (based on starting glycine) of sodium cocoyl glycinate (see table 1). The obtained product has a low viscosity. No additional solvent was added; all methanol mentioned in table 1 as "solvent" is from the sodium methylate solution.

Example 1b: Production of N-Acylated Amino Acids: Reaction of Glycine (=Amino Acid) with Coconut Oil (=Triglyceride) in the Presence of a Solution of Na-Methanolate in Methanol with Vacuum (Invention)

The reactor was charged with 64.8 g of a 25 wt % sodium methylate solution in methanol (0.3 mol sodium methylate)

and 22.5 g of glycine (0.3 mol) was added while stirring at 40° C. After homogenization 65.7 g of coconut oil (0.1 mol) was added and the temperature was raised to about 140° C. while methanol was distilling off. After removing 80 wt % of the theoretical amount of methanol vacuum was applied up to 300 mbar. After 2 hours of distillation, it was cooled down to 100° C., vacuum was removed, nitrogen inserted and water was added to prepare an aqueous solution of 35-40 wt % dry matter ("dry matter" means amount of solid product).

Example 2: Production of N-Acylated Amino Acids: Reaction of Glycine (=Amino Acid) with Coconut Oil (=Triglyceride) in the Presence of a Solution of Na-Methanolate in Methanol without Vacuum (Comparison)

Same procedure as Example 1 but vacuum was not applied. Total reaction time a raised to 5 h. Analysis is done by liquid chromatography and gave 48.1% yield (based on starting glycine) of sodium cocoyl glycinate.

Example 3: Production of N-Acylated Amino Acids: Reaction of Glycine (=Amino Acid) with Coconut Oil (=Triglyceride) in the Presence of a Solution of Na-Methanolate in Methanol and in Presence of Glycerol without Vacuum (Comparison)

Same procedure as Example 2 but 34.8 g (0.378 mol) of glycerol was added to the reaction start mixture. Vacuum was not applied. Total reaction time was 5 h. Analysis is done by liquid chromatography and gave 63.8% yield (based on starting glycine) of sodium cocoyl glycinate.

Example 4: Production of N-Acylated Amino Acids: Reaction of Na-Glycinate (=Salt of Amino Acid) with Coconut Oil (=Triglyceride) in the Presence of a Solution of Na-Methanolate in Methanol with Vacuum (Comparison)

The reactor was charged with 29.1 g of Na-glycinate (0.3 mol), 65.7 g of coconut oil (0.1 mol) and while stirring 6.48 g of a 25% sodium methylate solution in methanol (0.03 mol sodium methylate) and 43.7 g of methanol was added. While heating this heterogeneous mixture to 130-140° C., methanol is distilling off and can be condensed with a water-cooled condenser. The temperature at the head of the distillation bridge rises to 65° C. As the methanol removal approaches the end of the reaction, the temperature at the distillation bridge goes down and the product mixture is well stirrable. In order to remove methanol completely from the reaction mixture additionally vacuum of 100-300 mbar is applied and further methanol is distilling of. The reaction mixture is getting very viscous during this stage. After total of 3.5 h the vacuum is then removed by inserting nitrogen and the mixture is diluted with water to give a roughly 30% aqueous pale-yellow to orange clear solution of sodium cocoyl glycinate. The temperature goes down below 100° C. and the product can be cooled down to ambient temperature staying a good stirrable clear solution. Analysis is done by liquid chromatography and gave 67.3% yield (based on starting glycine) of sodium cocoyl glycinate.

Example 5: Production of N-Acylated Amino Acids: Reaction of Glycine (=Amino Acid) with Methyllaurate (=Methylester, No Triglyceride) in the Presence of a Solution of Na-Methanolate in Methanol and in Presence of Glycerol with Vacuum (Comparison)

The reactor was charged with 128.6 g of methyl laurate (0.6 mole), 45.0 g of glycine (0.6 mole) and while stirring 192.6 g of a 25% sodium methylate solution in methanol (0.6 mol sodium methylate) and 17.9 g of glycerol (0.194 mol) was added. While heating this heterogeneous mixture to 110-120° C., methanol is distilling off and can be condensed with a water-cooled condenser. The temperature at the head of the distillation bridge rises to 65° C. As the methanol removal approaches the end of the reaction, the temperature at the distillation bridge goes down and the product mixture is well stirrable. In order to remove methanol completely from the reaction mixture additionally vacuum of 100-20 mbar is applied and further methanol is distilling of. The reaction mixture is getting very viscous during this stage. After total of 4.5 h the vacuum is then removed by inserting nitrogen and the mixture is diluted with water to give a roughly 30% aqueous pale-yellow to orange clear solution of sodium lauroyl glycinate. The temperature goes down below 100° C. and the product can be cooled down to ambient temperature staying a good stirrable clear solution. Analysis is done by liquid chromatography and gave 25.8% yield (based on starting glycine) of sodium lauroyl glycinate.

Example 6: Production of N-Acylated Amino Acids: Reaction of Na-Glycinate (=Salt of Amino Acid) with Coconut Oil (=Triglyceride) in the Presence of a Calcium Oxide and Glycerol (Comparison; Analog to EP 2736878)

The reactor was charged with 35 g of Na-glycinate (0.36 mol), 82.4 g of coconut oil (0.125 mol), 0.8 g calcium oxide (0.014 mol) and 50 g glycerol (0.54 mol). While heating this heterogeneous mixture was reacted at 130° C. After total of 5 h the mixture is diluted with water to give a roughly 30% aqueous solution of sodium cocoyl glycinate. The temperature goes down below 100° C. and the product can be cooled down to ambient temperature staying a good stirrable solution. Analysis is done by liquid chromatography and gave 59.8% yield (based on starting glycine) of sodium cocoyl glycinate.

TABLE 1

| | Cocoyl glycinate | | | |
|---|---|---|---|---|
| Example | Invention Example 1a | Invention Example 1b | Comparison with-out vacuum Example 2 | Comparison without vacuum and with additional glycerol Example 3 |
| Molar ratio Triglyceride:Glycine | 1:3 | 1:3 | 1:3 | 1:3 |
| Solvent | Methanol | Methanol | Methanol | Glycerol |
| wt % Solvent | 31.8% | 31.8 | 31.8% | 25.0% |
| Alkali | Na-methylate | Na-methylate | Na-methylate | Na-methylate |

TABLE 1-continued

| | solution | solution | solution | solution |
|---|---|---|---|---|
| Catalyst | — | — | | |
| Vacuum | 300 mbar | 300 mbar | no | no |
| Reaction time [h] | 3 | 3 | 5 | 5 |
| Inner Temperature | 140° C. | 142° C. | 132° C. | 140° C. |
| Yield based on Glycine in % | 87.2 | 71.0 | 48.1 | 63.8 |

| | Cocoyl glycinate | | |
|---|---|---|---|
| Example | Comparison Na-Glycinate; no In-Situ Example 4 | Comparison C12-Methylester and with additional glycerol Example 5 | Comparison Na-Glycinate; with CaO + glycerol; see EP2736878 Example 3 Example 6 |
| Molar ratio Triglyceride:Glycine | 1:3 | ME-Ester:Glycerol 1:0.29 | 1:2.9 |
| Solvent | Methanol | Methanol | Glycerol |
| % Solvent calculated for complete reaction mixture | 33.5% | 30.2% | 29.7% |
| Alkali | Na-methylate solution as catalyst | Na-methylate solution | — |
| Catalyst | | | CaO |
| Vacuum | 300 mbar | 20 mbar | no |
| Reaction time [h] | 3.5 | 4.5 | 5 |
| Inner Temperature | 137° C. | 120° C. | 130° C. |
| Yield based on Glycine | 67.3 | 25.8 | 59.8 |

Table 1 shows that the yield of N-acylated glycinate prepared according to the invention example 1 is highest. Products obtained by processes without the in-situ produced salts (see comparison example 4), without vacuum (see comparison example 2), with other additional solvents (see comparison example 3), with other catalysts (see comparison example 6), with methyl esters instead of carboxylic glycerides (see comparison example 5) or in comparison to the known state of the art show clearly worse yields, even with longer reaction times in all comparison examples.

The invention claimed is:

1. A process for preparing a surfactant solution with an N-acyl amino acid or its salt comprising a) preparing an alkali metal salt of an amino carboxylic acid in-situ by reacting the amino carboxylic acid and an alkali metal methoxide by a1) reacting the amino carboxylic acid with a solution consisting of an alkali metal methoxide in methanol in presence of a carboxyl glyceride ester or by a2) reacting the amino carboxylic acid with a solution consisting of the alkali metal methoxide in methanol and afterwards adding the carboxyl glyceride ester before b) forming the N-acyl amino acid salt by reacting the alkali metal salt of the amino carboxylic acid with the carboxyl glyceride ester by heating and under removal of methanol until at least 60 wt % of a theoretical amount of methanol was removed and c) afterwards applying vacuum and d) after releasing vacuum adding water to form a solution with the N-acyl amino acid salt e) and optionally adjusting the pH value.

2. The process according to claim 1, wherein the amino carboxylic acid is selected from the group consisting of alanine, glycine, threonine, and asparagine.

3. The process according to claim 1, wherein in a) the alkali metal salt of the amino carboxylic acid is prepared by reacting the amino carboxylic acid in a relative mole ratio of amino carboxylic acid to alkali metal methoxide in a range from about 3:1 to 1:3.

4. The process according to claim 1, wherein the alkali metal salt of the amino carboxylic acid is prepared by a1) reacting the amino carboxylic acid with a solution consisting of the alkali metal methoxide in methanol in presence of the carboxyl glyceride ester.

5. The process according to claim 1, wherein in a) the alkali metal salt of the amino carboxylic acid is prepared by reacting the amino carboxylic acid with the alkali metal methoxide under stirring until homogenization.

6. The process according to claim 1, wherein the carboxyl glyceride ester is selected from a glyceride ester of fatty acid having 6 to 22 carbon atoms.

7. The process according to claim 1, wherein forming the N-acyl amino acid salt by reacting in b) is by the heating at a temperature above 100° C.

8. The process according to claim 1, wherein the alkali metal salt of the amino carboxylic acid is prepared from the alkali methoxide in methanol, wherein the alkali is selected from the group consisting of sodium and potassium.

9. The process according to claim 1, wherein the methanol in b) is removed under atmospheric air pressure.

10. The process according to claim 1, wherein the reacting in b) is carried out until at least 65 wt %, of the theoretical amount of methanol is removed.

11. The process according to claim 1, wherein a mole ratio of the alkali metal salt of amino carboxylic acid to the carboxyl glyceride ester is in the range of 0.9:1 to 1.1:1, based on the fatty acid of carboxyl glyceride ester.

12. The process according to claim 1, wherein in c) a vacuum is applied in a range of 100 to 400 mbar.

13. The process according to claim 1, wherein in d) the water is added to form a solution with the N-acyl amino acid acid or its salt in a range from 20 to 70 wt.

14. The process according to claim 1, wherein in step d) the water is added at a temperature in a range of 90 to 130° C.

15. The process according to claim 1, wherein in e) the pH value is adjusted after cooling.

16. The process according to claim 1, wherein no additional solvent or liquid is added.

17. The process according to claim 1, wherein no work-up follows to obtain the N-acyl amino acid salt.

18. The process according to claim 1, wherein a yield of obtained N-acyl amino acid or its salt is greater than 80 mol %, based on amino acids.

* * * * *